(12) United States Patent
Kline

(10) Patent No.: US 6,744,036 B2
(45) Date of Patent: Jun. 1, 2004

(54) OPTICALLY COUPLED SENSOR FOR APPLICATION TO COMBUSTIBLE LIQUIDS

(75) Inventor: Bruce R. Kline, Starksboro, VT (US)

(73) Assignee: Simmonds Precision Products, Inc., Charlotte, NC (US)

( * ) Notice: Subject to any disclaimer, the term of this patent is extended or adjusted under 35 U.S.C. 154(b) by 42 days.

(21) Appl. No.: 10/261,760

(22) Filed: Oct. 1, 2002

(65) Prior Publication Data
US 2004/0061043 A1 Apr. 1, 2004

(51) Int. Cl.$^7$ .................................................. G01J 1/04
(52) U.S. Cl. ............................. 250/227.21; 250/227.11; 250/551
(58) Field of Search ................... 250/227.21, 227.11, 250/208.2, 551, 900; 398/107, 109, 168, 171, 154; 340/521, 511, 531, 555

(56) References Cited

U.S. PATENT DOCUMENTS

| 4,820,916 A | 4/1989 | Patriquin |
| 4,963,729 A | 10/1990 | Spillman et al. |
| 5,223,707 A | 6/1993 | Bjork |
| 6,014,076 A | 1/2000 | Luzzader |

*Primary Examiner*—Thanh X. Luu
*Assistant Examiner*—Seung C Sohn
(74) *Attorney, Agent, or Firm*—Calfee, Halter & Griswold LLP; David R. Percio

(57) ABSTRACT

An optically coupled circuit is electrically coupleable to a capacitive probe transducer disposed in a liquid in a tank for sensing the capacitance of the probe transducer which is a measure of a parameter of the liquid. A first converter circuit receives optical energy over a non-conductive path and converts it into electrical energy at a predetermined voltage potential from which first and second reference voltage potentials are developed. A dual slope integrator circuit is coupleable to the probe capacitor for charging it during a first integration period and discharging it during a second integration period utilizing the first and second reference voltage potentials. The integrator circuit includes a circuit for comparing capacitive voltage generated during the first and second integration periods with the first and second reference voltage potentials to generate timing signals for each integration period. The timing signals from two successive integration periods are used for determining the capacitance of the probe transducer. A system and method of determining the probe capacitance are also disclosed.

30 Claims, 6 Drawing Sheets

TIME

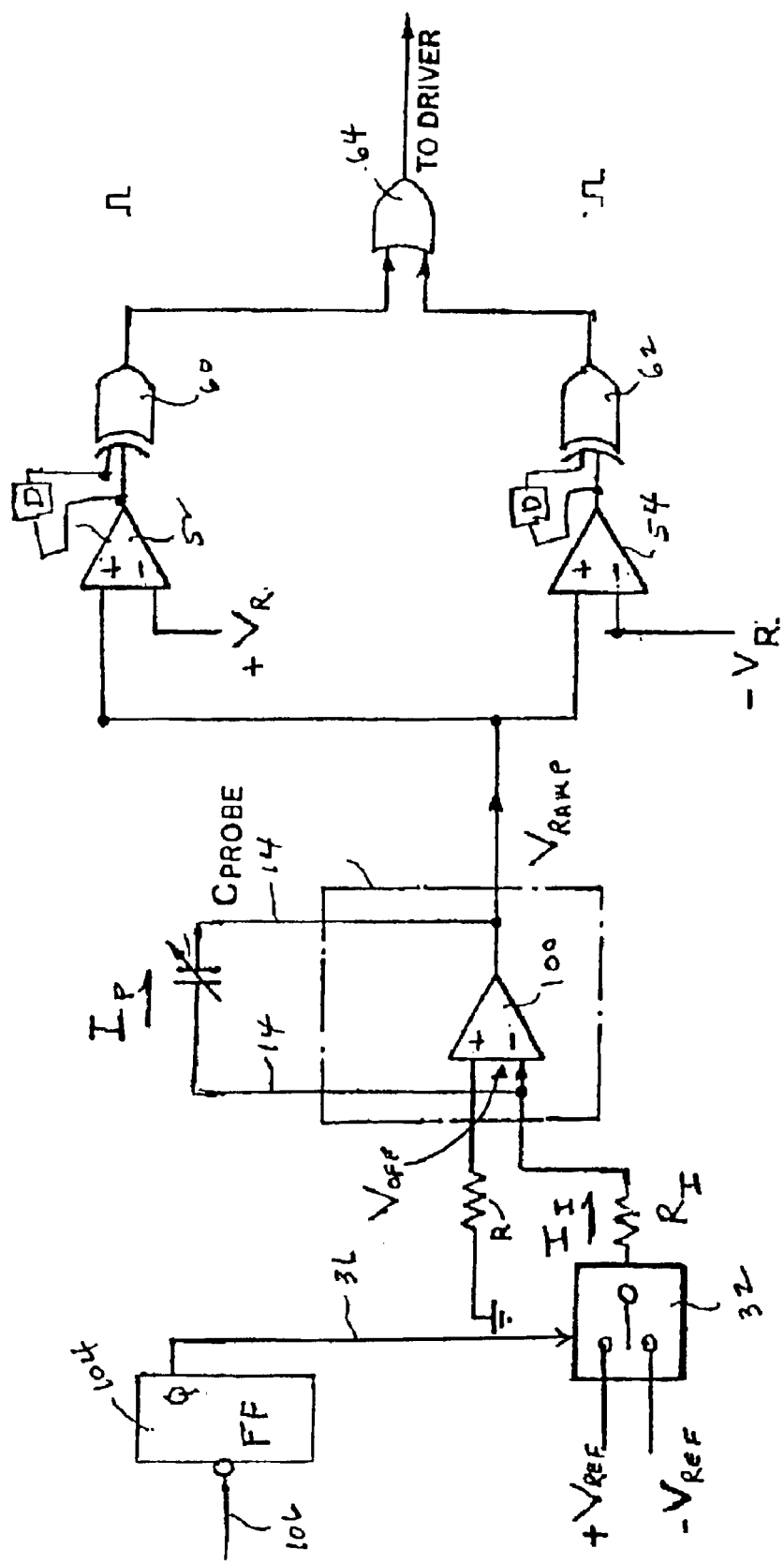

OPTICALLY COUPLED SENSOR FOR APPLICATION TO COMBUSTIBLE LIQUIDS

BACKGROUND OF THE INVENTION

The present invention is directed to optically coupled sensors for measuring a parameter of a combustible liquid, in general, and more particularly, to an optically coupled sensor using error self-correcting measurement techniques.

In general, conventional parameter measurement sensors for use in combustible liquids have been made intrinsically safe by transmitting power and control signals to and receiving measurement representative signals from the sensors over some non-conductive communication path, like an optical fiber path, for example. In the U.S. Pat. No. 4,963,729, issued Oct. 16, 1990 and entitled "Optically Powered Sensor System With Improved Signal Conditioning" which is assigned to the same assignee as the instant application, a conventional capacitive probe for measuring fuel level in an aircraft fuel tank is sensed using electronics at or near the probe which are optically coupled to a remote controller. The controller includes an optical source which provides optical energy to the probe electronics over an optical fiber path. The probe electronics converts the optical energy into electrical energy which is stored for powering the probe electronics. When optical power is interrupted, the probe electronics performs two measurements of the capacitance value of the probe using an integrator and two comparators, one with a reference capacitor and one without. Two spaced apart pulses are generated from the comparators with each measurement. Each set of pulses are converted to optical energy using a light emitting diode (LED), for example, which is transmitted back to the remote controller over the optical fiber path during the period of optical power interruption. Optical power is then resumed until the next measurement sample. The remote controller computes a compensated measurement of liquid level from the timing of the two sets of pulses received during the sampling period.

The present invention provides a precision measurement of probe capacitance with a minimum of power, complexity and cost for the probe electronics. It also lowers power of the probe electronics well within the twenty (20) microjoule safety limit for fuel tank use proposed by some airlines, and uses integration techniques to eliminate all offset error caused by the probe circuits. Accordingly, the optically coupled sensor of the present invention is much more accurate and stable and lower in cost than such sensors currently being used. Conventional probe placement and compensation for fuel measurement in a tank need not be altered for an embodiment of the present invention.

SUMMARY OF THE INVENTION

In accordance with one aspect of the present invention, an optically coupled circuit is electrically coupleable to a capacitive probe transducer disposed in a liquid in a tank for sensing the capacitance of the probe transducer which is a measure of a parameter of the liquid. The optically coupled circuit comprises: a first converter circuit for receiving optical energy over a non-conductive path and for converting the optical energy into electrical energy at a predetermined voltage potential; means for developing first and second reference voltage potentials from the predetermined voltage potential; a dual slope integrator circuit coupleable to the probe capacitor for charging the probe capacitor during a first integration period and discharging the probe capacitor during a second integration period utilizing the first and second reference voltage potentials, the integrator circuit including a circuit for comparing capacitive voltage generated during the first and second integration periods with the first and second reference voltage potentials to generate timing signals for each integration period; and means for determining the capacitance of the probe transducer as a function of timing signals from two successive integration periods.

In accordance with another aspect of the present invention, an optically coupled sensor system for measuring a parameter of a liquid in a tank comprises: a capacitive probe transducer disposable in the liquid, the probe capacitance being a measure of the liquid parameter; and an optically powered circuit electrically coupleable to the capacitive probe transducer for sensing the capacitance thereof The optically powered circuit comprises: a first converter circuit for receiving optical energy over a non-conductive path and for converting the optical energy into electrical energy at a predetermined voltage potential, the optically powered circuit being powered by the electrical energy; means for developing first and second reference voltage potentials from the predetermined voltage potential; a dual slope integrator circuit coupleable to the probe capacitor for charging the probe capacitor during a first integration period and discharging the probe capacitor during a second integration period utilizing the first and second reference voltage potentials, the integrator circuit including a circuit for comparing capacitive voltage generated during the first and second integration periods with the first and second reference voltage potentials to generate timing signals for each integration period; and a second converter circuit for converting the timing signals into optical signals for transmission over the non-conductive path. The system includes means coupleable to the non-conductive path for receiving the optical timing signals and determining the capacitance of the probe transducer as a function of timing signals from two successive integration periods.

In accordance with yet another aspect of the present invention, a method of determining the capacitance of a capacitive probe disposed in a liquid within a tank, the capacitance being used for measuring a parameter of said liquid, the method comprising the steps of: receiving optical energy from a non-conductive path; converting the optical energy to electrical energy at a predetermined voltage potential; developing first and second reference voltage potentials from the predetermined voltage potential; charging and discharging the probe capacitor during respective first and second integration periods utilizing the first and second reference voltage potentials; generating timing signals for each of the first and second integration periods utilizing the first and second reference voltage potentials; and determining probe capacitance using timing signals of two successive integration periods.

BRIEF DESCRIPTION OF THE DRAWING

FIG. 5 is a circuit schematic of the exemplary dual slope integration circuit showing greater detail.

DETAILED DESCRIPTION OF THE INVENTION

A method and apparatus is described herein below for measuring a parameter of a combustible liquid within a tank using conventional or other liquid parameter measuring capacitive probes. In one embodiment, the capacitive probe measurement apparatus does not include any wires or other conductors penetrating the wall of the combustible liquid tank (see illustration of FIG. 6). Rather, power is conducted optically to a probe electronics module which may be disposed at the probe, within the tank, which may be a fuel tank, for example. Other embodiments include probe electronics at the tank wall (see illustrations of FIGS. 7–8). The optical power for the probe electronics may be conducted over a non-conductive path, like an optical fiber link, for example. In the present embodiment, a short cessation or pulsed interruption of the optical power over the non-conductive path triggers the probe electronics to measure the capacitance of the probe which is configured within a dual slope integrator circuit.

The measurement method comprises charging and discharging the capacitance of the probe from a constant current source during first and second integration periods utilizing selected high and low reference voltages. During each integration period, the voltage across the probe capacitor changes linearly with a constant slope which is proportional to the value of the probe capacitance. The slope is measured by the generation of timing signals. In the present embodiment, two pulses are generated for each integration period; the pulses being triggered when the voltage across the probe capacitance crosses the high and low reference voltages. The direction of the charging current is reversed with each integration period by alternately selecting between the high and low reference voltages. For each integration period, the charging current is proportional to the selected reference voltage. Thus, the reference voltages do not need to be accurate. This process eliminates the step of resetting the voltage across the probe capacitance before a measurement is made. The timing pulses of each measurement are transmitted optically to a remote measurement or indicator circuit by way of an optical fiber, possibly, but not necessarily, the same optical fiber conducting the optical power. The timing between the two pulses is determined for each integration period or measurement. Averaging the pulse timing determined from any two successive integration periods eliminates all offset errors in the capacitance measurement. The only component affecting gain error in the present embodiment is one precision resistor used in the constant current source as will be better understood from the description found herein below.

Figure 1:
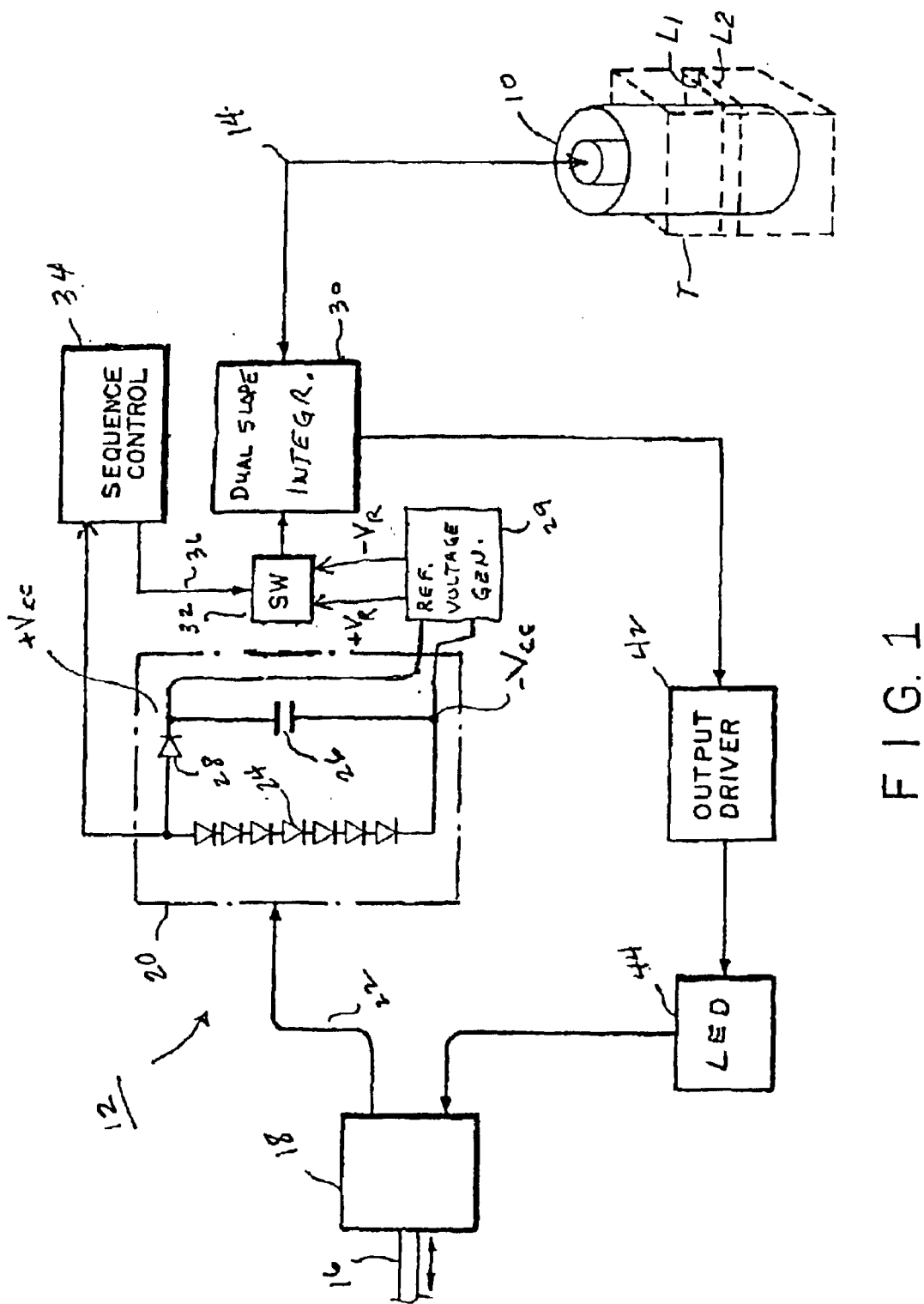
FIG. 1 is a block diagram schematic of an exemplary optically coupled sensor embodiment suitable for embodying the principles of the present invention.

An exemplary optically coupled sensor suitable for embodying the principles of the present invention is illustrated in the block diagram schematic of FIG. 1. In the present embodiment, a capacitive probe transducer 10 is disposed in a combustible liquid within a tank T, which may be a fuel tank of an aircraft, for example, to measure the level L1 or L2 of the liquid in the tank T or to measure the dielectric constant of the fuel with a totally immersed probe of known dimensions. Capacitance probes 10 are generally fabricated from conductive cylindrical sleeves that are concentrically mounted relative to each other to define capacitor plates, the capacitance of which changing with liquid level or dielectric constant of the liquid. Sensor electronics, shown at 12 in FIG. 1, are coupled to the transducer 10 over signal lines 14 for taking measurements of the capacitance of probe 10 during sampling periods as will become better understood from the following description.

In the present embodiment, optical energy from a remotely located optical source, like a laser diode, for example, may be provided to the sensor electronics 12 over a non-conductive path, like an optical fiber path or link 16, for example. The non-conductive optical path or link 16 may be a single optical fiber carrying optical power in one direction and the timing pulses in the other direction. If only one bi-directional fiber is used, then an optical coupler 18 is provided to combine and separate the optical power and timing pulses. Alternatively, two fibers may be included in path 16, one dedicated to delivering optical power to the probe electronics and the other for carrying the timing pulses from the probe electronics. In this embodiment, the optical coupler 18 may be eliminated.

At the sensor electronics 12, the optical energy is directed from the optical coupler 18 to a power converter 20 over an optical path 22. Within the power converter 20, the optical energy is directed to a series-connected array of photodiodes 24 which is in shunt circuit arrangement with a storage capacitor 26 and in series with a diode 28. In the converter 20, optical energy is converted by the photodiodes 24 to electrical energy in the form of a DC potential and stored in the capacitor 26. The diode 28 isolates the photodiodes 24 from the remainder of the sensor electronics. The above referenced U.S. Pat. No. 4,963,729 which is incorporated by reference herein will provide a more detailed description of a suitable remotely located optical energy source for powering the sensor electronics 12.

In the present embodiment, optical energy is converted to electrical energy by the illumination of the photodiode array 24. The array 24 may comprise six or seven photodiodes in series connection in order to develop sufficient DC voltage, say on the order of three to six volts, for example, across the storage capacitor 26 (taking into account the voltage drop of the isolating diode 28) for powering the sensor electronics 12. Each photodiode of the array 24 may be arranged so as to be substantially equally illuminated by the optical energy from the path 22. Alternatively, a single photodiode may be used to produce a voltage potential of about one volt, albeit at a higher current, and a conventional DC-DC converter coupled to the photodiode may be used to raise the voltage potential developed by the single photodiode to a level usable by the sensor electronics which may be three to six volts, for example. The photodiode array embodiment is considered smaller, easier to implement and more efficient.

Voltage potential developed across the capacitor 26 may be regarded as $+V_{CC}$ and $-V_{CC}$ with respect to a reference potential which may be half way therebetween and regarded as $V_{GND}$. In the simplest case, $-V_{CC}$ may be considered $V_{GND}$. In any event, these voltages are used to power the circuits of the probe electronics 12. In addition, the voltage potentials $+V_{CC}$ and $-V_{CC}$ may be provided to a voltage reference generator circuit 29 for deriving reference voltage potentials $+V_R$ and $-V_R$ which are provided to a dual slope integration circuit 30 via a multiplexer switch 32. Switch 32 couples the voltage potentials $+V_R$ and $-V_R$ at different times to the integration circuit 30 which is coupled to the capacitive probe 10 over signal lines 14. In addition, a sequence control circuit 34 monitors the optical power supplied to the converter 20 and responds to a change thereof (measurement request) by sending a ramp direction signal 36 to switch 32. Sequence controller 34 may be a memory circuit element that alternates state with each measurement request.

The integration circuit 30 is operative to develop positive and negative sloping voltage ramps, the slope of each being proportional to the capacitance of probe 10. From each ramp, the circuit 30 generates timing signals, which may be a set of two timing pulses, for example, which are converted to optical timing signals or pulses and conducted over the optical path 16 via an output driver circuit 42 and light emitting diode (LED) 44 to a remotely located controller unit (not shown). The timing between the two pulses is indicative of the capacitance value of the probe. A measurement of the liquid level L in the tank T may be computed at the remote controller based on the set of two pulses for each of two successive sampling periods as will become more apparent from the description supra. The U.S. Pat. No. 4,963,729 which has been incorporated by reference herein offers an embodiment of a remotely located controller unit suitable for use in the present embodiment.

Figure 2:
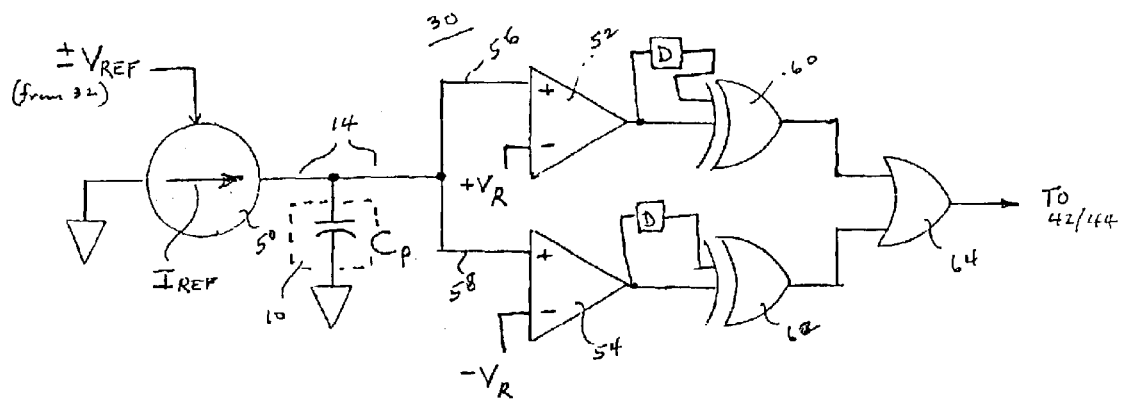
FIG. 2 is a circuit schematic of an exemplary dual slope integration circuit suitable for use in the sensor embodiment of FIG. 1.

A circuit schematic of a suitable embodiment for the dual slope integration circuit 30 for use in the sensor electronics 12 is shown by way of example in FIG. 2. Time graphs of FIGS. 3A, 3B and 4A–4C are provided for explaining the operation of the present embodiment. Referring to FIG. 2, a constant current source $I_{REF}$ is shown at 50 and provides current at times to the capacitor $C_P$ of the probe 10 over signal lines 14. The constant current source 50 may be driven by one or the other of the reference voltage potentials $\pm V_R$ via multiplexer switch 32 as controlled by the unit 34. The voltage potential across the capacitor $C_P$ is monitored by two comparators 52 and 54 via lines 56 and 58 which are coupled respectively to non-inverting (+) inputs of the comparators 52 and 54. An inverting (−) input of comparator 52 is coupled to the voltage potential $+V_R$ which may be derived from $+V_{CC}$ and an inverting (−) input of comparator 54 is coupled to the voltage potential $-V_R$ which may be derived from $-V_{CC}$. The outputs of comparators 52 and 54 may be coupled respectively to one input of exclusive OR gates 60 and 62 and coupled through a delay circuit D respectively to another input of the exclusive OR gates 60 and 62. Each of the delay circuits D may be comprised of a resistor-capacitor circuit or a plurality of gates in which the propagation delay of the gates create the time delay. The time delay determines the optical pulse width. To minimize power use, such pulses should be made as short as possible. The outputs of the gates 60 and 62 are coupled to inputs of an OR gate 64 the output of which being coupled to the driver-LED 42/44 as shown in FIG. 1.

Figure 3A:
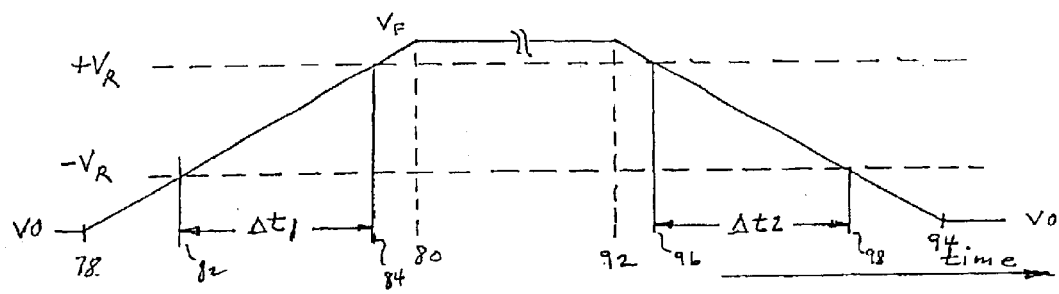
FIGS. 3A and 3B are time graphs for use in illustrating the operation of a dual slope integration circuit.

The operation of the dual slope integrator embodiment 30 will now be described in connection with FIGS. 1, 2, 3A, 3B, and 4A–4C. In the present embodiment, a brief interruption of optical power to the sensor electronics (see 70 and 72 in FIG. 4A) which may be on the order of less than 0.5 milliseconds, for example, is detected by the unit 34 for triggering the start of a sampling or measurement period. In response to the power interruption pulse 70, for example, the unit 34 may select the $+V_R$ potential via switch 32 for controlling the charging of the capacitor $C_P$ by the current source 50 as shown at time 76 in FIG. 4B. Thereafter, the charging of capacitor $C_P$ by the current source 50 commences at time 78 as shown in FIG. 3A. During this charging time, the voltage across $C_P$ ramps up from an initial voltage $V_0$ to a final voltage $V_F$ at time 80 at which time the charging ends (see FIG. 3A). Presuming that the voltages $+V_R$ and $-V_R$ remain constant during the course of a sampling period, the current source 50 shall also remain constant for the sampling period. Accordingly, because the same $+V_R$ and $-V_R$ are used to create the charging current and the comparator references, any errors in the reference voltages will be self-correcting and the value of the capacitor $C_P$ may be very accurately measured by determining the time between pulses of a measurement period.

In the present embodiment, the voltage ramp is measured by determining the times at which the ramp crosses or transitions through the two reference levels $-V_R$ and $+V_R$ by the comparators 54 and 52, respectively. The time interval $\Delta t$ that the voltage ramp takes to transition between the two reference voltages is exactly proportional to the unknown capacitance of the probe 10. More specifically, when the voltage ramp crosses $-V_R$ (see FIG. 3A), the output of comparator 54 changes state from low to high or 0 to 1 which causes the output of exclusive OR gate 62 to go from low to high momentarily until the delayed comparator output reaches the other input of the exclusive OR gate 62 (see pulse at time 82 in FIG. 4C). This momentary change of state or pulse generated at the output of the exclusive OR gate 62 is optically passed to the remotely located controller over optical fiber path 16 via OR gate 64, and driver/LED 42,44. Moreover, when the voltage ramp crosses $+V_R$ (see FIG. 3A), the output of comparator 52 changes state from low to high or 0 to 1 which causes the output of exclusive OR gate 60 to go from low to high momentarily until the delayed comparator output reaches the other input of the exclusive OR gate 60 (see pulse at time 84 in FIG. 4C). This momentary change of state or pulse generated at the output of the exclusive OR gate 60, which is preferably on the order of 0.5 microseconds or less, for example, is also optically passed to the remotely located controller over optical fiber path 16 via OR gate 64, and driver/LED 42,44. Thus, the remote controller has one set of pulses from which it may determine $\Delta t1$ for one sampling period. The remote controller may be a fuel quantity indicator which may be modified to house and control a laser diode optical power source and signal conditioning circuits for use with the present embodiment.

Figure 4A:
FIGS. 4A–4C are time graphs for use in illustrating the control sequencing of a dual slope integration circuit.
Figure 4B:
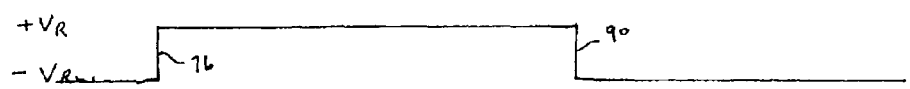
Figure 4C:

The foregoing described operation may be repeated for a successive second sampling period starting with the pulsed interruption of power at time 72. Note that with the commencement of the second sampling period, there is no resetting of the voltage of the capacitor $C_P$ which remains substantially at the final voltage level $V_F$ from the first sampling period. Also, at the commencement of the second sampling period at time 90 as shown in FIG. 4B, the unit 34 controls multiplexer switch 32 to select the voltage $-V_R$ for use by current source 50 and starts the discharge of the capacitor $C_P$ at time 92 as shown in FIG. 3A. The capacitor voltage is ramped down as shown in FIG. 3A through the current circuit 50 until it reaches the voltage level around the voltage $V_0$, for example, at time 94. During the ramp down period between times 92 and 94, the capacitor voltage will cross the voltage levels $+V_R$ and $-V_R$ at times 96 and 98, respectively. At such crossings, short pulses are generated as shown in FIG. 4C in the same manner as described for the ramp up operation herein above. This set of pulses 96, 98 is also optically passed to the remotely located controller over optical fiber path 16 via gate 64, and driver/LED 42,44. Thus, the controller has another set of pulses from which it may determine $\Delta t2$ for a second sampling period. By averaging the two successive pulse time differences, $\Delta t1$ and $\Delta t2$, all offset errors of the sensor electronics are removed and an accurate measurement of the probe capacitance, and thus, liquid level, may be obtained.

Figure 3B:
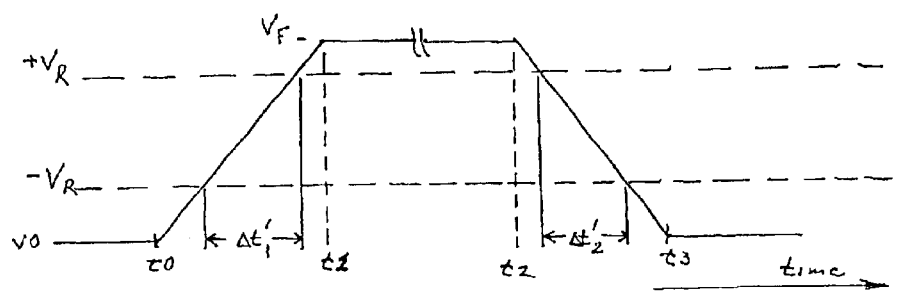

At a subsequent time, another two successive measurements may be made at a different liquid level which produces a lesser probe capacitance, for example, as shown in the time graph of FIG. 3B. Note that in the example of FIG.

3B, the charge and discharge ramp slopes between times t0–t1 and t2–t3 are steeper than those of the first example described in connection with the time graph of FIG. 3A. Accordingly, Δt1' and Δt2' will be shorter than Δt1 and Δt2. Again, by taking an average of Δt1' and Δt2', all of the circuit offset errors will be removed. In this manner, a measurement sampling rate of more than 100 per second may be achieved.

In the present embodiment, a commercially available communication style optical receiver may be disposed at the remote controller for converting the optical timing pulses to electrical pulses and commonly available digital circuits including a clock running at 10 MHz, for example, may measure the time between pulses (Δt) with more than adequate resolution and accuracy. However, while the timing signals of two successive measurements are separately transmitted to and combined in the remote controller for the present embodiment, it is understood that such combining could just as well take place in the probe electronics and a signal indicative of the combination or average of the timing signals transmitted back to the remote controller for determining the liquid parameter without deviating from the broad principles of the present invention.

The circuit schematic of FIG. 5 shows the dual slope integrator embodiment 30 in greater detail. Referring to FIG. 5, the constant current source 50 comprises a precision resistor $R_I$ coupled between the output of the switch 32 and an inverting (−) input of an operational amplifier circuit 100. The capacitive probe $C_P$ is coupled across the (−) input and output of the operational amplifier 100 via lines 14. A non-inverting (+) input of the amplifier 100 is coupled to a ground potential through a balance resistor R. In addition, a flip flop circuit 104 may be triggered by a signal 106 indicative of the optical power interruption pulse to toggle a Q output thereof which controls the setting of switch 32 to either $+V_R$ or $-V_R$ voltages which determines the direction of the slope of the voltage ramp.

The dual slope integrator circuit 30 of FIG. 5 operates much in the same manner as that described for the embodiment of FIG. 2. For example, for ramp up, the $-V_R$ is selected by the flip flop circuit 104 for the first sampling period and the capacitor $C_P$ is charged by the current $-V_R/R_I$. For ramp down, the $+V_R$ is selected for the successive second sampling period and the capacitor is discharged by the current $+V_R/R_I$. In both the ramp up and ramp down sampling periods, a set of pulses are produced as described infra for use in establishing the time differences Δt1 and Δt2 between pulse sets which are averaged to determine an accurate measurement of the capacitance. Note the $R_I$ is the only component of the probe electronics 12 that should be made precise since all other errors are offset errors and are eliminated by the dual slope integration. That is, all errors that may cause the up voltage ramp to be too long, for example, will cause the down voltage ramp to be too short by an equal amount and vice versa. Thus, averaging the Δts of any two consecutive measurements will cancel all offset errors.

In summary, the present embodiment of the optically coupled sensor is powered continuously with the optical signal except for very brief pulses of interruption (<0.5 msec.) to start the measurement sampling periods and thus, can tolerate significantly lower stored energy than current optically powered sensors. Such lower stored energy is substantially lower than the most stringent (20 microjoules) safety limit for fuel tank use proposed by some airlines. The lower stored energy, reduced circuit complexity, micro-powered circuitry and reduced costs are beneficial features of the present invention. Moreover, the gain accuracy of the sensor electronics is based on one precision resistor and the self-correcting dual slope integration techniques reduce noise and eliminate substantially all offset errors.

Figure 6:
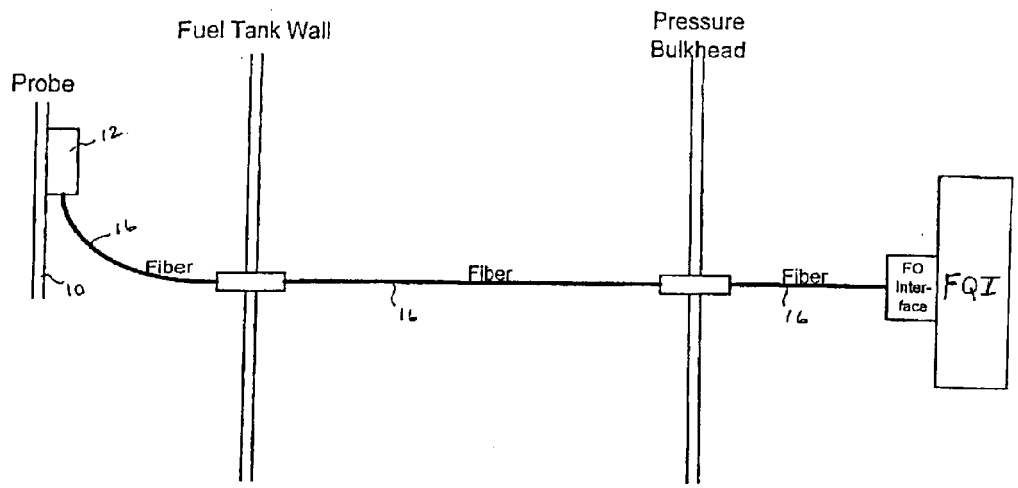
FIGS. 6, 7 and 8 are sensor system topologies for use in illustrating applications of an optically coupled sensor in accordance with other aspects of the present invention.
Figure 7:
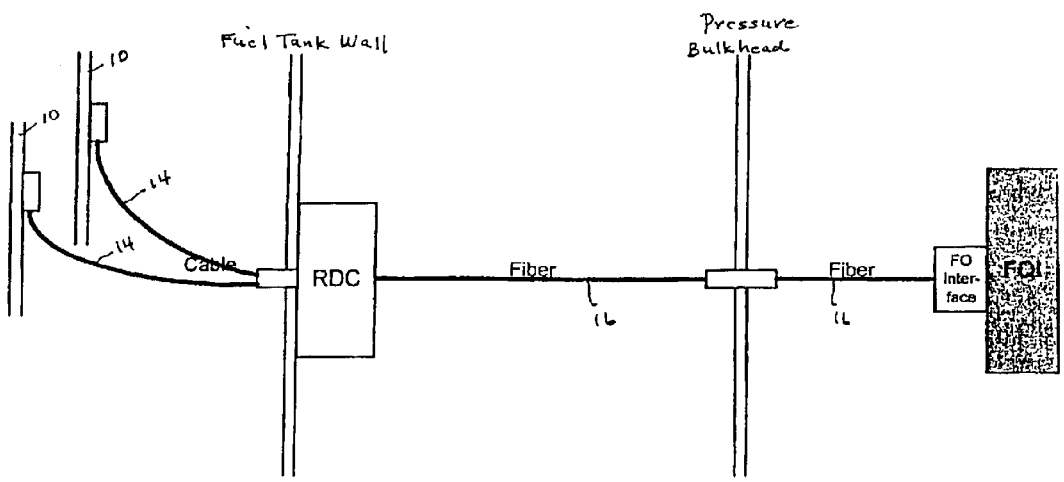
Figure 8:
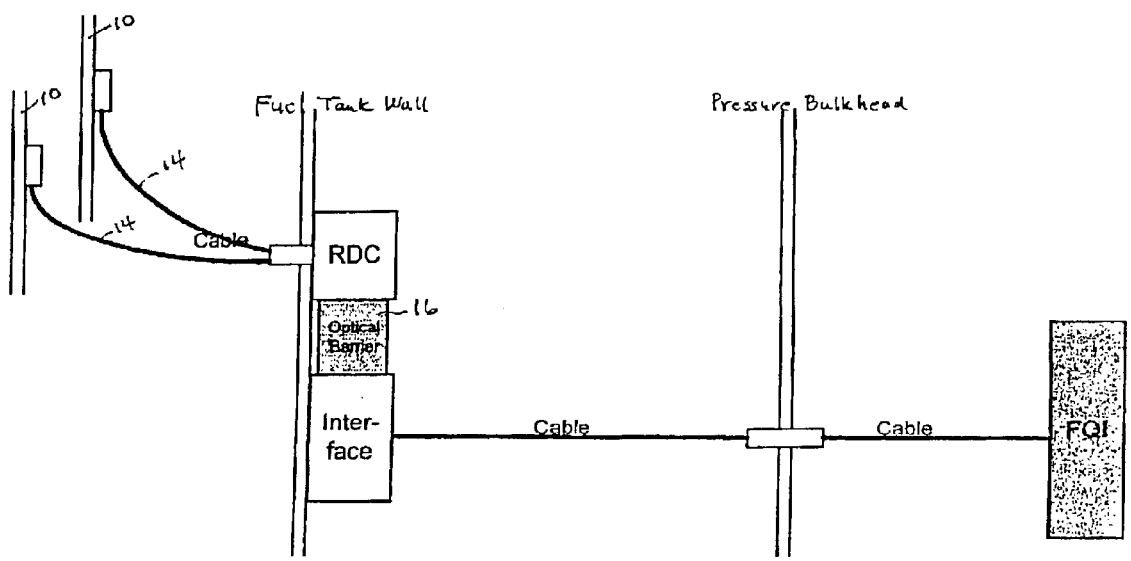

The present embodiment of an optically coupled sensor permits the use of many different system topologies as shown by the illustrations of FIGS. 6, 7 and 8. FIG. 6 illustrates how the present embodiment may be configured in an aircraft with optical fiber paths connecting a fuel quantity indicator (FQI) to the fuel level measurement probes 10 within the fuel tank. In this configuration, the probe electronics module 12 is disposed at the probe 10 within the fuel tank and the FQI includes the optical source for generating optical energy over the optical fiber path 16 to the module 12. In addition, the timing pulses are conducted optically form the module 12 over fiber optic paths 16 through the fuel tank wall and pressure bulkhead to a fiber optic (FO) interface at the FQI which includes circuitry for combining or averaging timing signals from two successive measurements to determine the probe capacitance. The probe capacitance measurement is used to compute the desired parameter of the liquid using processing circuitry in the FQI, for example. This configuration gives sufficient protection from lightning, electrical shorts, and high-intensity radio frequencies (HIRF) since there are no conductive paths into the fuel tank.

In the configuration illustrated in FIG. 7, the optically coupled electronics 12 may be moved from the fuel probe 12 within the tank and mounted on the fuel tank wall outside of the tank. This system topology would permit multiple probes 10 to be operated from one electronics module, a remote data concentrator (RDC), by multiplexing, for example. It would also allow existing probe wiring 14 inside of the fuel tank to be used to avoid changes to this hard to access area. In addition, although the optically powered electronics are very reliable because they do not generate any appreciable heat, they are accessible for repair without entering the fuel tank itself, which is a very desirable feature of this configuration. Careful design and placement of the RDC at the fuel tank wall would maintain a safety barrier to lightning, electrical shorts, and HIRF.

The optically powered techniques presented in this invention may be used to construct an intrinsic safety barrier as illustrated in the configuration of FIG. 8. This topology requires the least alteration to existing aircraft fuel measurement systems. Referring to FIG. 8, electrical cable is provided from the FQI through the pressure bulkhead to a FO interface at the tank wall. Power and timing signals may be conducted over an optical barrier to the probe electronics in the RDC. While many existing optical barriers exist, they apply only to signals, not power. The techniques of the present invention allows power as well as signals to optically pass the intrinsic safety barrier, the barrier can be complete and robust to any extreme degree. Similar to the configuration of FIG. 7, this configuration would also allow existing probe wiring 14 inside of the fuel tank to be used to avoid changes to this hard to access area.

While the present invention has been described above in connection with one or more embodiments, it is understood that such descriptions were presented merely by way of example and that there was no intention of limiting the present invention in any way, shape or form to any such embodiments. Rather, the present invention should be construed in breadth and broad scope in accordance with the recitation of the claims appended hereto.

What is claimed is:

1. An optically coupled circuit electrically coupleable to a capacitive probe transducer disposed in a liquid in a tank for sensing the capacitance of said probe transducer which is a measure of a parameter of said liquid, said optically coupled circuit comprising:

a first converter circuit for receiving optical energy over a non-conductive path and for converting said optical energy into electrical energy at a predetermined voltage potential;

means for developing first and second reference voltage potentials from said predetermined voltage potential;

a dual slope integrator circuit coupleable to said probe capacitor for charging said probe capacitor during a first integration period and discharging said probe capacitor during a second integration period utilizing said first and second reference voltage potentials, said integrator circuit including a circuit for comparing capacitive voltage generated during the first and second integration periods with said first and second reference voltage potentials to generate timing signals for each integration period; and means for determining the capacitance of the probe transducer as a function of timing signals from two successive integration periods.

2. The optically coupled circuit of claim 1 including a second converter circuit for converting the timing signals into optical timing signals for transmission over the non-conductive path.

3. The optically coupled circuit of claim 2 wherein the capacitance determining means is coupleable to said non-conductive path for receiving the optical timing signals and determining the capacitance of the probe transducer as a function of an average of the optical timing signals from two successive integration periods.

4. The optically coupled circuit of claim 1 including a control circuit for monitoring the optical energy received by the optically coupled circuit and operating the integrator circuit through first and second integration periods in response to interruptions in said optical energy.

5. The optically coupled circuit of claim 4 wherein the control circuit includes: a memory circuit triggered by the optical energy interruptions to switch between first and second output states; and a switch circuit governed by said first and second output states to select between the first and second reference voltage potentials to operate the integrator circuit through the first and second integration periods.

6. The optically coupled circuit of claim 1 wherein the comparing circuit includes: a first comparator circuit for generating a first pulse when the capacitive voltage generated during the first and second integration periods crosses the first reference voltage potential; and a second comparator circuit for generating a second pulse when the capacitive voltage generated during the first and second integration periods crosses the second reference voltage potential, a time difference between said first and second pulses being a measure of the probe capacitance.

7. The optically coupled circuit of claim 1 wherein the integrator circuit includes a closed-loop amplifier circuit with the probe capacitance being coupleable to a feedback path thereof; wherein integration current is provided to said closed-loop amplifier circuit through a precision resistor from a selected one of the first and second reference voltage potentials; and wherein an output of the closed-loop amplifier circuit is representative of the capacitive voltage.

8. An optically coupled sensor system for measuring a parameter of a liquid in a tank; said system comprising:

a capacitive probe transducer disposable in said liquid, said probe capacitance being a measure of said liquid parameter;

an optically powered circuit electrically coupleable to said capacitive probe transducer for sensing the capacitance thereof, said circuit comprising:

a first converter circuit for receiving optical energy over a non-conductive path and for converting said optical energy into electrical energy at a predetermined voltage potential, said optically powered circuit being powered by said electrical energy;

means for developing first and second reference voltage potentials from said predetermined voltage potential;

a dual slope integrator circuit coupleable to said probe capacitor for charging said probe capacitor during a first integration period and discharging said probe capacitor during a second integration period utilizing said first and second reference voltage potentials, said integrator circuit including a circuit for comparing capacitive voltage generated during the first and second integration periods with said first and second reference voltage potentials to generate timing signals for each integration period; and a second converter circuit for converting the timing signals into optical signals for transmission over said non-conductive path; and means coupleable to said non-conductive path for receiving said optical timing signals and determining the capacitance of the probe transducer as a function of timing signals from two successive integration periods.

9. The system of claim 8 wherein the non-conductive path comprises a fiber optic path.

10. The system of claim 8 wherein the optically powered circuit is disposable at the probe within the tank; wherein the receiving means is disposable outside of the tank and coupleable to the optically powered circuit within the tank over the non-conductive path.

11. The system of claim 10 wherein the receiving means includes an optical source for generating the optical energy over the non-conductive path.

12. The system of claim 11 wherein the non-conductive path comprises a bidirectional fiber optic path for carrying both the optical energy and optical timing signals; and wherein the optically powered circuit includes an optical coupler for providing the optical energy to the first converter circuit from the bidirectional fiber optic path and providing the optical timing signals over the bidirectional fiber optic path to the receiving means.

13. The system of claim 8 wherein the optically powered circuit is disposable outside of the tank and electrically coupleable to the probe capacitor within the tank through electrical conductors; wherein the receiving means is disposable outside of the tank and coupleable to the optically powered circuit over the non-conductive path.

14. The system of claim 13 wherein the optically powered circuit is disposable at a wall of the tank and electrically coupleable to the probe capacitor within the tank through an opening is said wall by electrical conductors.

15. The system of claim 13 wherein the receiving means includes an optical source for generating the optical energy over the non-conductive path.

16. The system of claim 15 wherein the non-conductive path comprises a bidirectional fiber optic path for carrying both the optical energy and optical timing pulses; and wherein the optically powered circuit includes an optical coupler for providing the optical energy to the first converter circuit from the bidirectional fiber optic path and providing the optical timing signals over the bidirectional fiber optic path to the receiving means.

17. The system of claim 8 including means for causing pulsed interruptions of the optical energy over the non-conductive path; and wherein the dual slope integrator circuit including means responsive to the pulsed optical energy interruptions to initiate alternately the first and second integration periods to generate corresponding timing signals for each integration period.

18. The system of claim 8 including a liquid quantity indicator; and wherein the liquid quantity indicator contains the receiving means.

19. The system of claim 18 wherein the liquid quantity indicator includes an optical source for generating the optical energy over the non-conductive path.

20. The system of claim 8 wherein the liquid comprises a combustible liquid.

21. The system of claim 8 wherein the tank is an aircraft fuel tank; and wherein the liquid comprises aircraft fuel.

22. The system of claim 8 wherein the liquid parameter being measured comprises liquid level.

23. The system of claim 8 wherein the liquid parameter being measured comprises liquid dielectric constant.

24. A method of determining the capacitance of a capacitive probe disposed in a liquid within a tank, said capacitance being used for measuring a parameter of said liquid, said method comprising the steps of:

receiving optical energy from a non-conductive path;

converting the optical energy to electrical energy at a predetermined voltage potential;

developing first and second reference voltage potentials from the predetermined voltage potential;

charging and discharging the probe capacitor during respective first and second integration periods utilizing the first and second reference voltage potentials;

generating timing signals for each of the first and second integration periods utilizing the first and second reference voltage potentials; and determining probe capacitance using timing signals of two successive integration periods.

25. The method of claim 24 wherein the step of determining includes determining probe capacitance by averaging the timing signals of two successive integration periods.

26. The method of claim 24 including converting the timing signals into optical timing signals for transmission over the non-conductive path.

27. The method of claim 26 including the step of determining the capacitance of the probe transducer as a function of an average of the optical timing signals from two successive integration periods.

28. The method of claim 24 including the steps of: monitoring the received optical energy; and charging and discharging the probe capacitor alternately during respective first and second integration periods in response to successive interruptions in the monitored optical energy.

29. The method of claim 28 including the step of alternately selecting between the first and second reference voltage potential from which to develop a constant current for charging and discharging the probe capacitor alternately during respective first and second integration periods in response to successive interruptions in the monitored optical energy.

30. The method of claim 28 including the steps of: generating a first pulse when the capacitive voltage generated during the first and second integration periods crosses the first reference voltage potential; generating a second pulse when the capacitive voltage generated during the first and second integration periods crosses the second reference voltage potential; and determining the probe capacitance as a function of a time difference between said first and second pulses of each of two successive integration periods.

* * * * *